United States Patent [19]

Fleming

[11] Patent Number: 4,666,425

[45] Date of Patent: May 19, 1987

[54] DEVICE FOR PERFUSING AN ANIMAL HEAD

[75] Inventor: Chet Fleming, St. Louis, Mo.

[73] Assignee: The Dis Corporation, St. Louis, Mo.

[21] Appl. No.: 809,949

[22] Filed: Dec. 17, 1985

[51] Int. Cl.⁴ ............................................ A61M 37/00
[52] U.S. Cl. ...................................... 604/4; 128/1 R
[58] Field of Search .................... 604/4, 5, 6; 128/1 R

[56] References Cited

U.S. PATENT DOCUMENTS

| | | | |
|---|---|---|---|
| 4,116,589 | 9/1978 | Rishton | 604/4 |
| 4,192,302 | 3/1980 | Boddie | 604/4 |
| 4,540,399 | 9/1985 | Litzie et al. | 604/4 |
| 4,583,969 | 4/1986 | Mortensen | 604/4 |

OTHER PUBLICATIONS

Robt. J. White, "Brain," pp. 655-674 in Organ Preservation for Transplantation, 2nd ed., Karon & Pegg, 1981.

The Tomorrow File, by Lawrence Sanders (1975), pp. 430-432 and 459-466.

Heads, by David Osborn (1985), pp. 108-110 and 146-147.

Primary Examiner—John D. Yasko
Attorney, Agent, or Firm—Patrick Kelly

[57] ABSTRACT

This invention involves a device, referred to herein as a "cabinet," which provides physical and biochemical support for an animal's head which has been "discorporated" (i.e., severed from its body). This device can be used to supply a discorped head with oxygenated blood and nutrients, by means of tubes connected to arteries which pass through the neck. After circulating through the head, the deoxygenated blood returns to the cabinet by means of cannulae which are connected to veins that emerge from the neck. A series of processing components removes carbon dioxide and add oxygen to the blood. If desired, waste products and other metabolites may be removed from the blood, and nutrients, therapeutic or experimental drugs, anti-coagulants, and other substances may be added to the blood. The replenished blood is returned to the discorped head via cannulae attached to arteries. The cabinet provides physical support for the head, by means of a collar around the neck, pins attached to one or more vertebrae, or similar mechanical means.

20 Claims, 3 Drawing Figures

DEVICE FOR PERFUSING AN ANIMAL HEAD

BACKGROUND OF THE INVENTION

This invention is in the fields of biochemistry, blood processing, and prosthetic devices.

In general, a 'prosthetic device' is any device which is designed to substitute for a missing or defective part of the body. Although many prosthetic devices such as artificial limbs are mechanical in nature, a variety of prosthetic devices have been developed which are capable of processing blood or performing other internal functions. Most of these devices are used by connecting them to an artery and a vein, so that blood will circulate through them. The following descriptions are intended to provide a basic introduction to each device described; for more extensive discussion, the reader should refer to the references listed, and to other references known to those skilled in the art. Complete citations for books and articles are provided below.

As used herein, terms such as 'body' 'patient,' and 'head' normally refer to research animals. However, it is possible that after this invention has been thoroughly tested on research animals, it might also be used on humans suffering from various terminal illnesses.

CARDIO-PULMONARY BYPASS DEVICES

Cardio-pulmonary bypass machines are commonly used during heart surgery, since it is difficult for a surgeon to operate on a beating heart. In an operation involving a bypass machine, the heart is temporarily stopped by chilling the heart with a cold fluid, clamping the aorta, and administering potassium chloride. Cannulae (which are specialized tubes having rigid or semi-rigid ends, usually made of plastic) are inserted into the superior and inferior vena cavae (major blood veins which normally carry deoxygenated blood to the heart) through an opening that is created in the right atrial wall of the heart. These cannulae carry blood with low oxygen content and high carbon dioxide content from the body to the bypass machine.

The blood usually passes through a heat exchanger which cools the blood. During most bypass operations, the body temperature of the patient is lowered to about 28 to 30 degrees Celsius, to slow down metabolism and reduce oxygen consumption by the organs.

The cooled blood enters an oxygenation chamber. The two most commonly used types of oxygenation chambers are called 'bubble' oxygenators and 'membrane' oxygenators. In a bubble oxygenator, gas containing oxygen and a relatively small percentage of carbon dioxide enters the bottom of the chamber and flows upward through the circulating blood, creating bubbles. Contact between the bubbles and the blood adds oxygen to the blood and removes carbon dioxide. Upon leaving a bubble chamber, the blood passes through a defoaming device.

Membrane oxygenators contain a membrane which separates the gas from the blood. Oxygen and carbon dioxide can diffuse through the membrane, allowing oxygen to displace carbon dioxide in the blood. Such devices are sold by several suppliers, including American Bentley, and Shiley Inc., both of Irvine, Calif. By eliminating the interface between blood and gaseous oxygen, membrane oxygenators tend to cause less denaturation of blood proteins and damage to blood cells than bubble oxygenators.

After the blood has been oxygenated, it flows to a pump, usually a 'peristaltic' pump (also commonly called a 'roller' pump). The blood is pumped to a suitable pressure, and it returns to the patient's body via a cannula which is inserted into the patient's aorta.

Several chemical parameters are usually measured during an operation involving a bypass machine, including dissolved oxygen content (expressed as pO), dissolved carbon dioxide content (expressed as pCO), acidity (expressed as pH), and potassium concentration (expressed as pK). If desired, other parameters (such as the concentration of glucose and other blood sugars) can also be measured. Each of those values can be increased or decreased by external manipulation if desired.

For additional information on cardio-pulmonary machines see, e.g., Utley 1982, Berger 1979, or Bregman 1977. For additional information on cardiac surgery see, e.g., Sabiston et al 1983, Cooley 1984, or Norman 1972.

WASTE PRODUCTS

As used herein, 'waste product' includes any molecule which is present at a concentration which causes a deleterious effect on a patient, or which is accumulating in a manner which indicates that it should be removed to avoid a deleterious effect on a patient. This category includes metabolites such as urea, proteins which have been degraded and have lost their desired activity, acid which is accumulating at levels which create acidosis symptoms, dead cells, and nutrients which are present at excessive concentrations.

A variety of devices have been developed which can be used to remove waste products from blood, including the following.

HEMODIALYSIS MACHINES AND OTHER MEMBRANE DEVICES

One category of devices which can be used to remove waste molecules from the blood involves the use of semi-permeable membranes which allow certain types of charged molecules to pass through them while retaining other molecules and blood cells. The most common example of such a device used to treat blood is a hemodialysis machine, often called an 'artificial kidney.' These machines remove urea and several other metabolites from the blood. They are most commonly used to treat people whose kidneys are injured or diseased.

Typically, blood flows from the patient to a dialysis machine via a catheter tube connected to a blood vein by means of a needle. The blood in the machine flows through a chamber where it contacts a membrane. The membrane is made of a material which has a positive charge. The positive charge attracts molecules with negative charges, such as urea. Urea molecules pass through the membrane and are collected and removed.

Blood cells do not pass through the membrane, since the pores in the membrane are too small. In addition, desirable molecules such as albumin do not pass through the membrane, because they are not negatively charged. After urea is removed, the remaining blood is returned to the patient's body via a second catheter and a needle.

For additional information on hemodialysis machines, see Nissenson 1984, Cogan et al 1985, or Drukker et al 1983. For additional information on other types of membrane devices see, e.g., Buck 1982.

AFFINITY COLUMNS

A second type of device which is often used to remove components from biological fluids is often referred to as an 'affinity column.' In general, the term 'affinity binding' is used to refer to binding reactions between molecules which are attracted to each other (usually by electrical charges), but which do not form covalent bonds; see, e.g., Cuatrecasas et al 1971. An important type of affinity binding involves the binding that occurs between antigens and antibodies.

Methods are known for generating antibodies which will bind to virtually any type of protein or other large molecule; see, e.g., Schreier 1980. Briefly, this involves injecting the molecule into an animal, usually a mouse or rabbit. The animal's natural defense against infections will recognize the molecule as foreign. Certain types of blood cells in the animal (called lymphocytes) will secrete antibodies which bind to the foreign molecule. The antibodies are present in high concentration in a body fluid called 'ascites fluid', which is removed from the animal. The antibodies are concentrated and attached to a 'support' (usually small particles or a polymeric gel). The support with the antibodies is then immobilized inside a reaction vessel; for example, the inlet and outlet of the tube are packed with filter material (such as glass wool) that allows a fluid such as blood to pass through without allowing the support material or the antibodies to pass through. When blood is passed through the vessel, molecules which bind to the antibodies will remain in the column (stuck to the immobilized antibodies) while the remainder of the fluid passes through the leaves the vessel.

When the vessel begins to get saturated with waste molecules (as indicated by the passage of too many waste molecules through the column), the flow through the vessel is stopped, and the conditions inside the vessel are changed (for example, by the addition of salt or acid to a desired concentration). Under the changed conditions, the antibodies release the waste molecules, which are flushed out of the vessel by fluid flow and discarded. This effectively regenerates the antibodies, which can be used many times.

When ascites fluid is removed from an animal, it contains a mixture of 'polyclonal' antibodies which bind to different antigenic molecules. If desired, 'monoclonal' antibodies can be created which bind to a single antigenic molecule, by a different process. Briefly, this process involves removing numerous lymphocyte cells from the animal. Each different lymphocyte cell secretes a single type of antibody. The lymphocytes are joined or 'fused' to cancerous cells, by means of a chemical such as polyethylene glycol which causes cell walls to become soft. Each hybrid cell which survives the fusion process is called a 'hybridoma' cell. It will secrete a single type of antibody (because of the antibody generating gene it received from the lymphocyte cell), and it will reproduce itself indefinitely in a flask if nutrients are supplied to it (because of the uncontrolled growth genes it received from the cancer cell). The mixture of hybridoma cells is then tested to select a cell which generates the desired type of antibody. The selected hybridoma cell will generate identical, or 'monoclonal' antibodies; see, e.g., Schreier 1980. Monoclonal antibodies can be immobilized on a support, loaded into affinity columns, and used to remove specific molecules from blood or other fluids.

IMMOBILIZED ENZYME REACTION VESSELS

The third category of device which is used to remove undesired molecules from biological fluids involves enzymes. In general, enzymes are proteinous molecules which catalyze chemical reactions; see, e.g., Lehninger 1983 or Stryer 1980. Most enzymes are highly specific; they will catalyze only one reaction, which may involve joining together two molecules, cleaving a certain molecule into two smaller molecules, etc. Some enzymes are less specific; for example, some oxidase enzymes can add oxygen atoms to a wide variety of molecules. Enzymes are present in all living cells. most of the biochemical reactions in the body and the blood are controlled, either directly or indirectly, by enzymes. Molecule(s) that are transformed by enzymes are called 'substrate' molecules. Many enzymes are named by adding the suffix 'ase' to the name of a substrate or a reaction; for example, lipase enzymes cleave lipids, protease enzymes cleave proteins, and glucose phosphotransferase adds phosphate groups to glucose molecules.

It is possible to treat blood outside of the body by passing it through vessels (often called 'extracorporeal' vessels) which contain enzymes that are immobilized yet active. The following example, involving heparin and heparinase, is derived fSrom Langer et al 1982 and U.S. Pat. No. 4,373,023; also see Lavin et al 1985.

Heparin is a substance which is used by doctors in some situations to prevent blood from clotting; for example, it is often used during heart surgery to prevent blood from forming clots in a cardio-pulmonary bypass machine. However, heparin also inhibits the ability of the patient to form normal, healthy blood clots. The presence of heparin in treated blood can have harmful effects, such as causing hemorrhaging and blood loss, especially is used with injured patients.

Heparinase is an enzyme which catalyzes the inactivation (by cleavage) of heparin molecules. Langer et al developed a device containing immobilized heparinase, as follows. Heparinase molecules were conjugated (i.e., covalently bonded) to a solid 'support' in a way that does not prevent their enzymatic activity. The solid support consisted of a permeable material such as small particles or a polymeric gel. The support material with the heparinase was loaded into a vessel and held in place by filter material at the inlet and outlet of the vessel. Blood which contained heparin (to simulate blood which has flowed through a cardio-pulmonary machine) entered the vessel through the entrance filter, and contacted the immobilized heparinase molecules. The heparin molecules inthe blood were cleaved and inactivated by the heparinase. The blood left the vessel through the exit filter, and flowed to a pump.

Antibody columns and immobilized enzyme vessels would suffer from plugging up if not specially handled, due to the blood cells present in the fluid. To avoid this problem, Langer et al developed a method of keeping the support material inside the vessel stirred up and fluidized, to prevent clogging. This method involved continuously removing support material from one area of the vessel, and pumping it to a different area of the vessel.

The science of immobilizing enzymes is fairly well developed; see, e.g., U.S. Pat. No. 4,331,767 (Nakajima et al 1982). By the proper selection of support material, activating or crosslinking agents, and reaction parameters, it is possible to immobilize most types of enzymes in a reaction vessel without destroying their enzymatic activity.

Enzymes and/or bacterial cells have been identified and isolated which can degrade virtually any type of biological molecule.

NUTRIENTS

As used herein, 'nutrients' includes all molecules which help to maintain or restore metabolic activity when present at a proper concentration in the blood, or which are otherwise added to the blood of a patient in a therapeutic or research effort. This includes carbohydrates, vitamins, amino acids, nucleotides, blood proteins, substances involved in cyclic biochemical reactions, compounds added to the blood to sustain the proper pH, etc. It also includes pharmaceutical or experimental drugs. It does not include antibodies, or dissolved gases such as oxygen or carbon dioxide.

Nutrients are discussed in numerous texts on biochemistry; for example, Stryer 1980 and Lehninger 1983 are good introductory texts, while Lehninger 1975 is more complex and comprehensive.

DEVICES FOR ADDING NUTRIENTS TO BLOOD

A variety of devices and methods are known for adding any desired substance to a fluid in a desired concentration. For example, a substance may be pumped directly into the fluid at a desired rate, it may be allowed to diffuse out of a permeable holding device and diffuse into the fluid, or it may be allowed to pass through a membrane into the fluid. Various devices have been developed which allow sustained release of selected drugs into the blood stream at low concentrations for weeks or months after injection or implantation in an animal; see, e.g., Williams 1969 or Nixon 1976.

In addition, a variety of methods are known for monitoring the concentration of virtually any chemical substance in a fluid (see, e.g., Buck 1982), and for controlling the rate of addition of a substance to a fluid based upon the existing concentration of the substance.

BLOOD-COMPATIBLE MATERIALS

Various types of blood-compatible materials have been developed for catheters, prosthetics, and other medical uses. Such materials include various rigid or flexible plastics, and various metallic alloys. Blood compatible materials for any specific use must satisfy several requirements, which can vary depending upon the particular use. In general, a blood compatible device must not cause clotting of the blood, it must withstand leaching, corrosion, or other degradation by body fluids, and it must have sufficient strength, flexibility, and durability for its intended use. For more information on blood-compatible materials, see, e.g., Gebelein 1983 and Hench et al 1984.

PUMPING

A variety of different types of pumping systems have been developed for different uses. 'Peristaltic pumps', also called 'roller pumps', are used most commonly to pump fluids containing living cells, because they inflict very little stress or damage on cells; see, e.g., Norman 1972. In a peristaltic pump, blood or other fluid is contained inside a flexible tube, and a roller device is used to squeeze the tube in a manner such that the point of constriction moves along the length of the tube. The squeezing action forces fluid through the tube in the desired direction, and the fluid never touches anything except the inside of the tube. As mentioned above, peristaltic pumps cause very little turbulence or shear force in the fluid being pumped, which means that they inflict relatively little damage on blood cells when they are used to pump blood.

If desired, peristaltic and other pumps can be used to create pulsatile flow which resembles the pulsing action of heartbeats; see, e.g., U.S. Pat. No. 3,892,628 (Thorne et al, 1975).

BLOOD VESSELS

The main arteries that supply blood to the head are the carotid arteries and the vertebral arteries. There is a left common carotid, which branches directly off the aorta, the main artery leading from the heart. There is also a right common carotid, which comes from the aorta via an intermediate artery, called the innominate artery or brachiocephalic trunk. Both of the common carotids divide into internal and external carotids, up inside the neck. The left and right vertebral arteries branch off of subclavian arteries and travel to structures in the spine, where they move up to the base of the brain. They join together at the base of the brain in an artery called the basilar artery. An arterial structure supplied by several arteries at the base of the brain is called the Circle of Willis. If any of the arteries which supply the Circle of Willis are disrupted, the other arteries can supply sufficient blood to the brain.

The major veins that take deoxygenated blood from the head to the heart are the jugular, cervical, and vertebral veins. There are four jugular veins; both the left and the right side have internal and external jugular veins, which join larger veins near the heart. There are also deep cervical and vertebral veins, each of which come from a veinous network at the base of the brain next to the spinal cord, called a cervical plexus. If one of those veins is disrupted, the other vein can continue to drain the plexus.

A significant portion of the tissue in the face and neck is supplied by numerous small blood vessels that pass through the neck, which are not in direct communication with the arteries and veins mentioned above.

The capillaries inside the brain do not have the same type of porosity as the capillaries in the rest of the body. This is because the endothelial cells in the brain capillaries are joined by 'tight junctions,' whereas the same cells in other capillaries are separated by 'slit-pores.' The result is often referred to as the 'blood-brain barrier,' which prevents certain types of molecules from diffusing from the circulating blood into the brain.

For information on vascular surgery and microsurgery see, e.g., Haimovici 1984 and Daniel et al 1977.

CEREBROSPINAL FLUID

The entire cavity which contains the brain and spinal cord of an adult human has a volume of about 1650 ml. About 150 ml is occupied by cerebrospinal fluid. About 800 ml of fluid is formed each day by the ventricles in the brain; excess fluid is absorbed into the venous blood through the arachnoidal villi.

Excess fluid inside the skull is usually referred to as 'hydrocephalus.' It is often treated by inserting a semi-permanent 'shunt' (i.e., a drainage tube) into one of the ventricles, to drain the excess fluid into the peritoneal cavity, where it is absorbed.

TISSUE CULTURE SYSTEMS

As used herein, 'tissue culturing' refers to a process of growing and/or maintaining animal cells in a dish, flask, or other container outside of the body. Tissue culture using human cells can be done to study the cells, or to generate proteins or other products from the cells.

There are several important factors that affect tissue culture, including the following. First, animal cells are generally divided into two categories of cells. One category, known as 'suspension cells', includes cells which can reproduce while floating freely in liquid, unattached to any other cells or any solid surface. The most common example of suspension cells are white blood cells (since red blood cells do not contain chromosomes, they do not reproduce in culture). The second category is known as 'anchorage dependent cells'. This reflects the fact that most cells which make up cohesive tissue such as muscle, skin, or organs will not reproduce unless they can attach to other cells or certain types of artificial surfaces. Most cells taken from skin, liver, pancreas, or other tissue are anchorage dependent cells. Anchorage dependent cells can be cultured on the insides of tiny hollow tubes (see, e.g., U.S. Pat. No. 4,201,845, Feder et al, 1980) or on the surfaces of tiny particles which are floating in a liquid (see, e.g., U.S. Pat. No. 4,293,654, Levine et al, 1981).

The second major factor which affects tissue culture relates to the number of generations of cells which will reproduce outside the body. Usually, only a limited number of generations will grow from cells taken from non-tumorous tissue. The number of generations can vary, depending on cell type and other factors, but it is not uncommon for cells to stop reproducing after about twenty generations, regardless of what types of nutrients are supplied to them. Such cells are often referred to as a 'strain' of cells. By contrast, cells taken from cancerous tissue will usually reproduce indefinitely if supplied with suitable nutrients. Such cells are often referred to as 'immortal' cells, or as a cell 'line'.

Most types of non-cancerous cell strains can be converted into immortal lines by one of two processes. One process, which is usually called 'transformation' of the cells, involves the use of an organic virus such as the 'Epstein-Barr' virus. The other process involves fusing the cells with a cancerous cell line. Although either process will alter the genetic makeup of the cell, it is possible to select cells which have retained the desired characteristics (such as the continued expression of enzymes normally found in that type of tissue).

U. S. Pats. Nos. 4,060,081 (Yannas et al, 1977) and 4,280,954 (Yannas et al, 1981), describe the use of lattices derived from collagen, the protein which holds cells together in human tissue. Such lattices were developed to provide a suitable synthetic covering for burn wounds. Cells from the periphery of the burn wound, or cells that were implanted in the lattice (see U.S. Pat. No. 4,458,678, Yannas et al 1984) will grow in the pores in the lattice, creating new skin. Cells taken from other types of tissue, such as liver tissue, can also grow in such a lattice.

Another branch of technology which is related to tissue culture involves immobilized cells or tissue which are not actively reproducing, but which are enzymatically active. For example, Nose et al 1977 describes an artificial liver created by placing slices of liver in a perfusion chamber, and U.S. Pat. No. 4,353,888 (Sefton 1982) describes a method of encapsulating mammalian cells.

ORGAN PERFUSION

Intact organs can be preserved and studied using a specialized type of tissue culture, called technique of 'perfusion'. The greatest milestone in the history of perfusion research occured in 1938, with the publication of *The Culture of Organs* by Charles Lindbergh (the aviator) and Alexis Carrel.

One type of perfusion involves killing a laboratory animal, removing the organ(s) of interest, and maintaining the intact organs in a state which allows all or part of their metabolic activity to continue for a period of several hours or more. Such organs are usually submerged in a solution of buffered salt water, and blood or a blood fraction may be circulated through them if desired. By isolating an organ, scientists make it accessible for more direct observation, and they eliminate the variables caused by other organs in an intact animal. Another type of perfusion involves the preservation of organs (such as kidneys) from people who have been killed in accidents until they can be transplanted into other people.

Perfusion technology (in general, and on several specific organs) is described in Norman et al 1968, Berger 1979, and in various patents classified in U.S. class 435, subclass 283.

BRAIN PERFUSION

Research on perfused monkey brains is described in White et al 1968. As mentioned therein, there was a substantial drop in electroencephalic activity within three hours after the brain was removed from the skull, if no effort was made to remove metabolites from the circulating blood or add fresh blood fractions to the blood. If the blood which circulated through the brain was also circulated through the body of a second monkey, the period of 'viability' could be extended to more than 24 hours; see White et al 1967.

White et al 1968A described work which involved isolating the brain of a donor monkey and placing that brain in the skull of a recipient monkey in order to assess how long the brain would survive. There was no attempt to connect the brain to the sensory organs or spinal cord of the recipient monkey, or to regain normal functioning of the brain. The transplanted brains remained 'viable' for more than 3 days.

TRANSPLANTED HEADS

White 1971A describes two distinct surgical projects. In the first, a section of the neck of a rhesus monkey was removed. This operation completely severed the spinal cord and all nerves and tissue except for the carotid arteries and jugular veins, which served as the only remaining links between the head and the body. After that operation, each of the six monkeys operated on awakened and remained conscious during the period of study (eight hours). At the end of the study period, each monkey was painlessly killed for further analysis. In the second project, three primate heads (referred to as 'cephalons') were completely severed from thier bodies and transplanted onto the bodies of other monkeys, which remained intact. All of the transplanted heads regained consciousness for the study period (24 hours).

White 1971B describes a somewhat different procedure. Four rhesus monkeys were 'cervically transected' to remove their intact heads from their bodies. Each head was transplanted onto the body of a different monkey, which had been decapitated. All four transplanted heads regained consciousness, which lasted up to 36 hours. Hemorrhaging problems were encountered, attributed to chronic heparinization.

SPINAL CORD INJURIES

In general, a person or animal can survive total loss of spinal cord functioning, so long as the injury occurs below the intresection where the nerves that control respiration join the spinal cord.

If a nerve bundle in the spinal cord is 'divided' (severed by cutting, as is often done during neurosurgery to relieve severe chronic pain), the portion of the nerve bundle which remains connected to the brain does not carry any impulses to the brain. This leads to a feeling of numbness in the part of the body which was previously serviced by that nerve bundle.

It is possible to permanently inactivate nerve cells in the spinal cord by injecting them with certain substances (such as ethyl alcohol), or to temporarily alleviate pain by means of analgesic drugs such as morphine.

For information on spinal cord functioning, injuries, and research, on phantom pain, and on neurosurgery, see, e.g., Youmans 1982 and Wilkins 1985.

SUMMARY OF THE INVENTION

This invention relates to a device, referred to herein as a 'cabinet,' which will provide physical and biochemical support for an animal's head which has been 'discorporated' or 'discorped' (i.e., severed from its body). This device can be used to supply a discorped head with oxygenated blood and nutrients, by means of tubes connected to arteries which pass through the neck. After circulating through the head, the deoxygenated blood returns to the cabinet by means of cannulae which are connected to veins that emerge from the neck. A series of processing components will remove carbon dioxide and replenish the oxygen level in the blood, and return the replenished blood to the discorped head via cannulae attached to arteries. If desired, waste products and other metabolites may be removed from the blood, and nutrients, therapeutic drugs, experimental drugs, and other substances may be added to the blood.

The cabinet will provide physical support for the head, by means of a collar around the neck, pins or other devices attached to one or more vertebrae, or similar mechanical means. If desired, the spine may be left attached to the discorped head.

The support provided to the discorped head will prolong various natural metabolic activities in the head after it has been severed from the body. This will allow various types of analyses to be performed on the head (including pharmaceutical, toxicological, hormonal, and neurological analysis) without being affected by various metabolites generated by digestive and other internal organs when such analyses are performed on intact animals.

The severed head preferably should retain all of the sensory organs, and the vocal cords if desired. Depending on the surgical procedures used to sever the head from the body and the type of blood processing and drugs used during and after the operation, the discorped head might experience a period of consciousness after it has been severed from the body.

DETAILED DESCRIPTION OF THE INVENTION

This invention relates to a device for maintaining metabolic activity in a mammalian head which has been severed from its body. The components of this device comprise a unit referred to herein as a cabinet. The cabinet includes various types of blood processing and monitoring equipment, and it may be attached to an external control panel or other accessory devices if desired.

The head of a laboratory animal such as a chimpanzee or rhesus monkey may be severed from the body and coupled to the cabinet described herein, using means known to experimental surgeons. After this invention has been thoroughly tested on lab animals, it might also be possible to use this invention on terminally ill persons, subject to various government approvals and other legal requirements.

Figure 1:
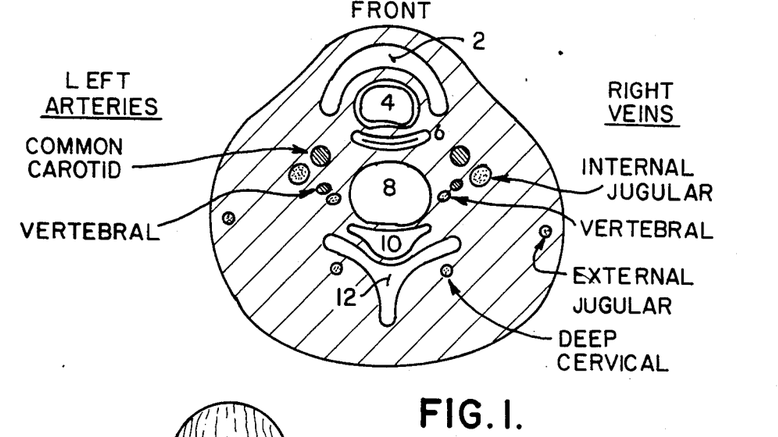
FIG. 1 is a cross-sectional depiction of the neck showing the major arteries and veins passing through the neck.

The major arteries and veins that pass through the neck of a primate are shown in FIG. 1. That figure also shows, for orientation, thyroid gland 2, trachea 4, esophagus 6, vertebral body 8, spinal cord 10, and spinous process 12. The four major arteries are the left common carotid, the left vertebral, the right common carotid, and the right vertebral. There are also eight major veins; each side has internal jugular, vertebral, external jugular, and deep cervical veins.

Each blood vessel may be severed and attached to a cannula (a specialized tube used in surgery). The specific location of each cut may be varied along the length of the blood vessel. The attachment may be made by ordinary techniques; for example, a cannula may be inserted into the end of a severed artery and the artery may be sutured directly to the cannula, or it may be sutured in a manner which constricts the artery around an enlarged ring near the end of the cannula. Alternatively, the vessels may be attached by means of temporary or semi-permanent coupling devices which do not require suturing.

When an operation has been completed, the arterial cannulae will carry oxygenated blood from the cabinet to the arteries, which will carry the blood into the head. Each severed vein will be attached to a veinous cannula which will carry deoxygenated blood from the head to the cabinet. Each cannula may be attached to the cabinet either directly or by means of an intermediate device such as a flow control manifold. At the completion of an operation. If desired, valve or choke devices may be provided in any cannula to ensure that the blood pressure in each vessel remains at a suitable level.

Figure 2:
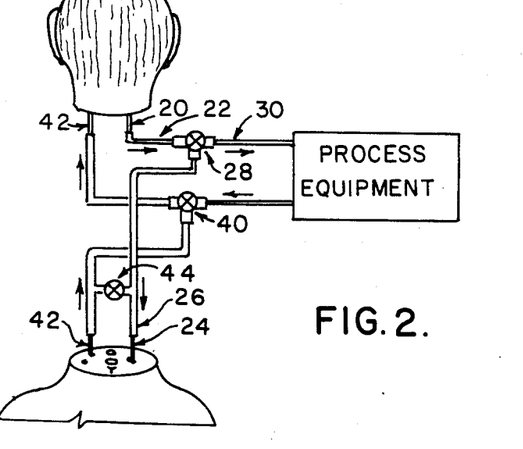
FIG. 2 depicts an arrangement for transferring blood flow from the heart to the device of this invention.

One method of transferring the blood vessels to the cabinet is shown in FIG. 2. In this figure, the internal jugular vein is clamped at two locations and severed between the clamps. The encephalic end 20 (i.e., the end which is attached to the head) is coupled to cannula 22, and the thoracic end 24 (the end which remains attached to the body) is coupled to cannula 26. Cannulae 22 and 26 are attached to T-valve or Y-valve 28, as is cannula 30 which leads to the blood processing equipment of this invention. In other words, T-valve 28 and two of its cannulae are inserted into the internal jugular vein. Similarly, T-valve 40 is inserted into the common carotid artery 42. When the valves are initially inserted, they allow blood to continue flowing through the vein or the artery. After both valves have been inserted, they are operated to redirect the blood to the processing equipment. At the same time, valve 44 is opened; it serves as a shunt which allows the heart to continue pumping normal volumes of blood, providing the remainder of the head with a continuous supply while the remaining vessels are being transferred to cannulae. This also provides approximately steady-state blood flow through the processing equipment. This procedure can be used as soon as valves have been inserted into one common carotid and one internal jugular, or after all four such valves have been inserted. If desired, the blood of the animal may be cooled during the operation to reduce oxygen consumption in the brain, as is commonly done during open heart surgery.

In addition to the major veins and arteries shown in FIG. 1, a number of smaller blood vessels carry blood to and from the face and neck. Any such blood vessel may be severed and attached to a cannula or to a manifold which leads to or from the cabinet. Capillaries and other very small vessels may be cauterized.

When deoxygenated blood enters the cabinet through the veinous cannulae, it passes through various pumps and treatment chambers as described below and indicated in FIG. 3. Each fluid-handling component is connected to fluid conduits in a manner such that when a severed head is couple to the device by means of the veinous and arterial cannula, the entire system is capable of circulating blood through each component and through the head.

It is anticipated that any waste products which are to be removed from the blood preferably should be removed before any nutrients are added; however, the exact sequence of treatment and pumping steps is not critical, and may be varied and optimized using routine experimentation.

Figure 3:
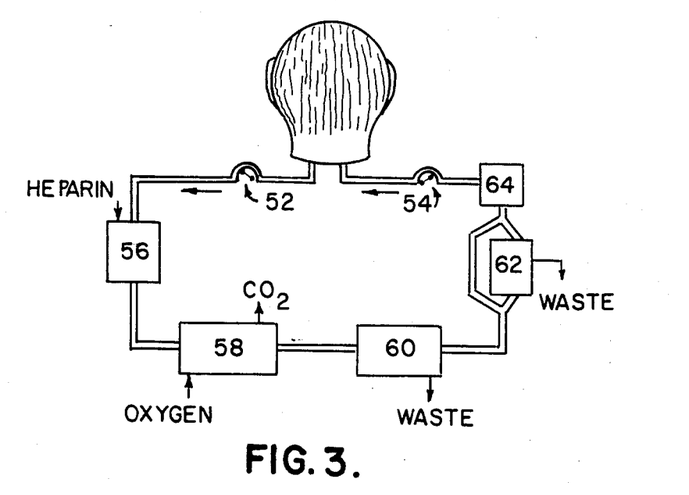
FIG. 3 is a schematic diagram depicting various pumping and treatment steps used in this invention.

The cabinet may be equipped with pumps at various locations, such as pumps 52 and 54 shown in FIG. 3. Such pumping should be performed by devices of a selected type which causes relatively low levels of damage to blood cells and other blood components, such as peristaltic (roller) pumps or multiple finger pumps. Proper sizing of a pump is a matter of routine calculation or experimentation. If desired, the pumps may be used to supply pulsatile flow which emulates the surges created by heartbeats. Exact location of the pumps is variable, so long as sufficient pressure is provided to cause the blood to flow through all treatment devices and through the head at satisfactory flow rates.

If desired, the cabinet may be equipped with one or more optional preliminary treatment chambers, such as chamber 56 shown in FIG. 3. In such chambers, the blood may be treated in various ways. For example, heparin may be added to the blood to prevent clotting; the blood may be heated or cooled in order to raise or lower the solubility of desired or undesired components; buffering compounds may be added to prevent wide swings in acidity or other processes which might damage cells or sensitive molecules; and the blood may be pumped to a desired pressure to cause it to flow through the subsequent components.

In oxygenation chamber 58, the blood is contacted with a gas that contains molecular oxygen, such as purified oxygen or air. If desired, the gas may be filtered or otherwise treated to reduce the risk that it will contain viruses or bacteria. This chamber can incorporate any of the components (including heat exchangers, anti-foaming devices, sensors, etc.) that are used by existing cardiopulmonary bypass machines. Preferably, the oxygenation chamber should use a membrane device, rather than a bubble or disk device, to minimize exposure of the blood to free gas interfaces.

Since the head does not contain any digestive or other internal organs, it generates waste products at a relatively low level compared to an intact animal body. This is highly advantageous with respect to the present invention. If desired, certain types of neurological, pharmaceutical, or other metabolic activity in a discorped head may be studied for a substantial peiod of time without suffering from high levels of interference by undesired metabolites. However, for long term study of the head, it is possible to reduce the level of any specific waste product or other metabolite in the blood by means of adding fresh blood to the system, or by treating the circulating blood to remove metabolites from it.

Waste products generated by metabolism inside the head (or added to the blood during processing) can be removed in one or more waste removal chambers, such as chamber 60 shown in FIG. 3. Depending on the type of molecule(s) being removed, such chambers can use any suitable selected mechanism. For example, urea and certain other nitrogenous compounds can be removed by membrane filtration, using devices comparable to hemodialysis meachines. Specific proteins and other large molecules can be removed by affinity binding, using devices such as stirred vessels containing monoclonal antibodies bound to small particles. Certain types of ionic substances may be removed by ion exchange devices. Certain molecules can be degraded by immobilized enzymes that are constrained within various types of vessels. It is possible to immobilize any desired number of different enzymes independently on compatible supports, and then combine the immobilized enzymes in a single vessel. Alternatively, if two enzymes do not function satisfactorily in the same vessel, it is possible to place them in separate vessels. For the purposes of this invention, a substance is regarded as removed from the blood if it is converted into a different substance; for example, heparin is removed from the blood when it is cleaved into two or more molecules which do not function as anti-coagulants, regardless of whether those smaller molecules remain within the blood.

If desired, the circulating blood may be separated into fractions (e.g., plasma) by means such as centrifugation, or into portions by means of a T-valve or Y-valve. If desired, a selected fraction or portion of the blood may be treated by any of the methods described herein and circulated through the cabinet and/or the head, without treating the remainder of the blood in a comparable manner. For example, all of the blood can be sent through the oxygenation chamber, while only a fraction or portion of the blood might be sent to a device such as affinity column 62 by using a parallel flow system.

The circulating blood may be processed in one or more optional tissue culture chambers which contain viable cells. For example, liver cells contain a complex mixture of enzymes which conjugate undesired molecules to electronegative molecules such as oxygen or glutathione. Such conjugation reactions usually increase the solubility of the undesired molecule in water, and allow the undesired compounds to be removed by other organs, primarily the kidneys. To simulate this natural process, a reaction vessel containing viable liver cells (either growing in culture, or obtained from cadavers) can be placed upstream of a hemodialysis device. Alternately, a mixture of liver enzymes can be immobilized inside a reaction vessel which is placed upstream of a hemodialysis device.

The blood (or a fraction or portion thereof) may be circulated through the body of a second lab animal (or possibly a brain-dead human). This can be accomplished by injecting the blood into a vein of the animal and collecting it from an artery. The intact body will process the blood through its liver and kidneys, and will remove various metabolites and add various nutrients and other molecules.

If heparin is added to the blood to prevent coagulation inside the processing equipment, it preferably should be removed from the blood before the blood is returned to the head if long-term support of the head is desired; otherwise, heparin tends to induce bleeding. Heparin removal chamber 64 can be similar to the device described in Langer 1982.

Any arterial or veinous cannula may pass through a manifold, an adjustable constriction, or a comparable flow control system to ensure that the rate of blood flowing through that cannula and through the connected blood vessel remains at approximately physiological levels. However, the varying internal diameters of the blood vessels will tend to serve that function even in the absence of a mechanical flow control system.

The equipment should be primed (filled with a suitable fluid, such as blood, plasma, or Ringer's lactate) before any connections are made between the head and the cabinet. During the surgical operation, it is possible to transfer arteries and veins which carry comparable amounts of blood to their cannulae in a balanced manner. This will allow the intake and output of blood from the cabinet to remain approximately balanced during the operation.

If desired, the circulating blood may be diluted, supplemented, or replaced by various substances. Suitable substances might include blood plasma or serum, Ringer's lactate, dextran, and blood substitutes such as certain types of fluorinated hydrocarbons.

The cabinet may be equipped with various devices to monitor certain chemical concentrations in the blood at any desired step during the processing of the blood. Devices and methods which measure the concentration of virtually and substance that is of interest are known to those skilled in the art of blood chemistry. Certain types of monitors (such as thermometers, pressure gauges, and electrodes) function continuously while remaining in contact with the blood. Such monitors do not add any undesired chemicals to the blood, and they may be positioned at any desired location in the cabinet. However, some types of chemical or biological analyses require samples of blood to be removed from the system and treated with chemicals which should not be circulated through the head. To allow for such chemical and biological analyses, sampling ports may be provided at any desired location to allow quantities of blood to be removed from the cabinet and analyzed.

Various control devices may be used to add any desired nutrient or other substance to the blood, to keep the affected blood values within desired (normally physiological) limits, or to conduct any particular type of experimentation. Any substance which is soluble in blood can be added by means of various pumping or diffusion devices.

If desired, the monitoring and control devices may be coupled to each other to provide for automated control of one or more blood parameters. For example, a pH monitor which generates an electronic signal may be placed in contact with the blood. This signal may be directed to a visual display, and to an electronic circuit which allows the signal to control the output of an acidity control device. If the signal indicates that the acidity of the blood is approaching an undesirably high level, the control device can activate a pump which will add an alkaline or buffering substance to the blood. It is possible to operate numerous automated control systems simultaneously, each of which can be directed toward controlling one or more parameters.

The cabinet is equipped with means for mounting the head in a position such that the veins and arteries which emerge from the head can be connected to the veinous and arterial cannulae. This can be accomplished by means such as inserting one or more surgical pins into the vertebrae in the neck, or by immobilizing the neck with an inflatable or padded collar. Preferably, the collar should be securely fitted around the neck to reduce the chance of infection at the exposed subcutaneous area at the base of the neck. If desired, the cabinet may be equipped to allow the head to be inclined in any direction, for ease of access during surgery.

If desired, the exposed subcutaneous area at the base of the neck may be covered with a flap of skin which remains attached to the neck during the operation, or by a synthetic membrane which controls moisture flux and reduces the chance of infection. For example, a bilayer membrane comprising a collagen-glycosaminoglycan lattice and a layer of silicone rubber, as described in U.S. Pat. No. 4,060,081 (Yannas et al, 1977) may be seeded with skin cells taken from the same patient, as described in U.S. Pat. No. 4,418,691 (Yannas et al, 1981). It may be cut to fit the exposed base of the neck with holes allowing the arteries and veins to pass through it, and sutured onto the exposed base of the neck near the end of the operation. The skin cells seeded into the membrane will grow to confluence, creating a new layer of skin, and the silicone layer will spontaneously detach from the new layer of skin.

The nerve signals from the body to the head may be terminated or reduced by severing the nerve bundles in the spinal cord, by injecting the nerves in the spinal cord or elsewhere with a nerve-killing substance such as ethyl alcohol, or by the use of analgesic (pain-reducing) drugs. If desired, the spine may remain attached to the head during the discorp operation, and enclosed in a sheath device which may contain circulating blood or a dielectric fluid.

If desired, the surgical cuts may be made in such a manner that the larynx (which contains the vocal cords) remains attached to the head. The severed end of the trachea (wind pipe) may be sutured to a tube carrying slightly compressed, humidified air, so that the primate or human head may use its vocal cords if it is conscious. The compressor may be controlled by a switch mounted below the chin of the head, so that the animal or human may turn the compressor on or off by opening its mouth.

In addition, the head may be severed from the body in such a manner that various organs contained in the neck or upper chest may remain attached to the head. Such organs include the thymus gland (which is involved in generating antibodies to help fight infections), the thyroid gland (which is involved in iodine metabolism and metabolic rate regulation), and the parathyroid gland (which is involved in regulating blood calcium concentration). In addition, the vocal cords may remain attached to the trachea, and a compressor may be provided which can pump humidified air into the severed lower end of the trachea, allowing the vocal cords to be operated. If desired, the compressor may be activated by a switch mounted beneath the jaw of the head, and the cabinet may be equipped with means for humidifying the air before or after it is compressed.

A shunt may be placed in one of the ventricles in the brain to drain excess cerebrospinal fluid.

The device of this invention can be manufactured and sold, and it may be used for various purposes such as analysis of drugs which are metabolized by the liver into undesiried compounds or which cannot cross the blood-brain barrier.

Those skilled in the art will recognize, or may ascertain using routine experimentation, numerous equivalents to the specific embodiments described herein. Such equivalents are within the scope of the claims.

I claim:

1. A device for maintaining metabolic activity in a mammalian head which has been severed from its body at its neck, comprising the following components:
   a. veinous cannulae which are capable of being attached to veins which pass through the neck and receiving blood from the veins;
   b. arterial cannulae which are capable of being attached to arteries which pass through the neck and transporting blood into the arteries;
   c. an oxygenation device which is in fluid communication with the veinous and arterial cannulae, and which is capable of displacing carbon dioxide contained in the blood with oxygen;
   d. one or more pumps of a selected type which causes relatively low levels of damage to blood components;
   e. fluid conduits which are attached to each of the components listed above in a manner such that the components, when coupled to the veins and arteries of a severed head by means of the cannulae of parts (a) and (b), will form a system capable of circulating blood through the oxygenation device and through the head after the head has been severed from the body; and,
   f. means for securely mounting the head upon the device after the head has been severed from the body, in a position such that the veins and arteries which emerge from the head can be connected to the veinous and arterial cannulae.

2. A device of claim 1 comprising at least one device or inlet port suited for allowing the addition of a nutrient, drug, anti-coagulant, or other desired substance to the blood at a desired concentration.

3. A device of claim 1 comprising at least one monitoring port which allows the measurement of selected physical or chemical characteristics of the blood at selected locations in the device.

4. A device of claim 1 comprising one or more components which can remove one or more waste products from the blood.

5. A method of claim 4 wherein the component which can remove waste products from the blood is selected from the group consisting of hemodialysis devices, affinity chromatography devices, ion exchange devices, immobilized enzyme vessels, and immobilized cell vessels.

6. A device of claim 1, wherein the oxygenation device comprises a membrane oxygenator.

7. A device of claim 1 which comprises a component designed for removing an anti-coagulant from the blood.

8. A device of claim 1 wherein the pumps are selected from the group consisting of peristaltic pumps and multiple finger pumps 9. A device of claim 1 which is equipped with one or more heat exchangers.

10. A device of claim 1 which is equipped with monitors for measuring blood temperature, blood pressure, oxygen content, carbon dioxide content, and acidity.

11. A device of claim 1 comprising a control system containing:
   a. a monitor designed for evaluating one or more blood parameters, which generates a variable electronic signal which depends on the value of the parameter being measured;
   b. a control device which is capable of generating an output which can affect the value of the parameter being measured; and,
   c. an electronic circuit which allows the electronic signal from the monitor to control the output of the control device.

12. A device of claim 11 comprising a multiplicity of feedback control systems capable of simultaneously regulating a multiplicity of different blood parameters.

13. A device of claim 1 comprising a flow control system designed for regulating the rate of blood flowing into each of the arterial cannulae.

14. A device of claim 1 which is equipped with an an outlet port designed for directing blood which is passing through the device, or a fraction or portion of such blood, to the body of a second animal, and an inlet port designed for receiving blood from the body of the second animal.

15. A device of claim 1 which is equipped with a compressor suitable for compressing air, and a conduit which can be coupled to a trachea.

16. A device of claim 15 which contains means for humidifying the air.

17. A device for maintaining metabolic activity in a mammalian head which has been severed from its body at its neck, comprising the following components:
   a. veinous cannulae which are capable of being attached to veins which pass through the neck and receiving blood from the veins;
   b. arterial cannulae which are capable of being attached to arteries which pass through the neck and transporting blood into the arteries;
   c. an oxygenation device which is in fluid communication with the veinous and arterial cannulae, and which is capable of displacing carbon dioxide contained in the blood with oxygen;
   d. one or more pumps of a selected type which causes relatively low levels of damage to blood components;
   e. one or more components which can remove one or more waste products from the blood;
   f. fluid conduits which are attached to each of the components listed above in a manner such that the components, when coupled to the veins and arteries of a severed head by means of the cannulae of parts (a) and (b), will form a system capable of circulating blood through the oxygenation device and through the head after the head has been severed from the body;

f. at least one monitoring port which allows the measurement of selected physical or chemical characteristics of the blood at selected locations in the device;

g. at least one device or inlet port suited for allowing the addition of a nutrient, drug, anti-coagulant, or other desired substance to the blood at a desired concentration; and, h. means for securely mounting the head upon the device after the head has been severed from the body, in a position such that the veins and arteries which emerge from the head can be connected to the veinous and arterial cannulae.

18. A device of claim 17 which comprises a component designed for removing an anti-coagulant from the blood.

19. A device of claim 17 which is equipped with an an outlet port designed for directing blood which is passing through the device, or a fraction or portion of such blood, to the body of a second animal, and an inlet port designed for receiving blood from the body of the second animal.

20. A device of claim 17 comprising a feedback control system containing:

a. a monitor designed for evaluating one or more blood parameters, which generates a variable electronic signal which depends on the value of the parameter being measured;

b. a control device which is capable of generating an output which can affect the value of the parameter being measured; and, c. an electronic circuit which allows the electronic signal from the monitor to control the outpur of the control device.

* * * * *